United States Patent [19]

Elgebaly

[11] Patent Number: 5,091,404

[45] Date of Patent: Feb. 25, 1992

[54] METHOD FOR RESTORING FUNCTIONALITY IN MUSCLE TISSUE

[76] Inventor: Salwa A. Elgebaly, 22 Silo Way, Bloomfield, Conn. 06002

[21] Appl. No.: 593,073

[22] Filed: Oct. 5, 1990

[51] Int. Cl.$^5$ .......................................... A61K 31/415
[52] U.S. Cl. .................................................. 514/401
[58] Field of Search ........................................ 514/401

[56] References Cited

PUBLICATIONS

Chem. Abst.-107 (1987), 5298R.
Chem. Abst.-111 (1989), 106699j.
G. R. Griffiths and J. B. Walker—Accumulation of Analog of Phosphocreatine in Muscle of Chicks Fed 1-Carboxymethyl-2—iminoimidazolidine (Cyclocreatine), Journal of Biological Chemistry, vol. 251, pp. 2049-2054 (1976).
T. M. Annesley and J. B. Walker—Cyclocreatine Phosphate as a Substitute for Creatine Phosphate in Vertebrate Tissues. Energetic Considerations, Biochemical and Biophysical Research Communications, vol. 74, pp. 185-190 (1977).
J. B. Walker—Creatine: Biosynthesis, Regulation, and Function, Advan. Enzymol., vol. 50, pp. 177-242 (1979).
T. M. Annesley and J. B. Walker—Energy Metabolism of Skeletal Muscle Containing Cyclocreatine Phosphate—Delay in Onset of Rigor Mortis and Decreased Glycogenolysis in Response to Ischemia or Epinephrine, Journal of Biological Chemistry, vol. 255, pp. 3924-3930 (1980).
J. J. Roberts and J. B. Walker—Feeding a Creatine Analogue Delays ATP Depletion and Onset of Rigor in Ischemic Heart, J. Physiol., vol. 243, pp. H911-H916 (1982).
J. J. Roberts and J. B. Walker—Synthesis and Accumulation of an Extremely Stable High—Energy Phosphate Compound by Muscle, Heart, and Brain of Animals Fd the Creatine Analog, 1-Carboxyethyl-2-Iminoimidazolidine (Homocyclocreatine), Archives of Biochemistry and Biophysics, vol. 220, pp. 563-571 (1983).
Lary A. Robinson, M. D., Mark V. Braimbridge—Creatine phosphate: An Additive Myocardial Protective and Antiarrhythmic Agent in Cardioplegia, vol. 87, pp. 190-200 (1984).
D. M. Turner and J. B. Walker—Relative Abilities of Phosphagens with Different Thermodynmic or Kinetic Properties to Help Sustain ATP and Total Adenylate Pools in Heart During Ischemia, Archves of Biochemistry and Biophysics, vol. 238, pp. 642-651 (1985).
J. Roberts and J. B. Walker-Higher Homolog and N—Ethyl Analog of Creatine as Synthetic Phosphagen Precursors in Brain, Heart, and Muscle, Repressors of Liver Amidinotransferase, and Substrates for Creatine Catabolic Enzymes, Journal of Biological Chemistry, vol. 260, pp. 13502-13508 (1985).
M. L. Semenovsky, M.D., V. G. Sharov, M.D., G. M. Mogilevsky, M.D., A. V. Asmolovsky, M.D., L. A. Makhotina, Ph.D. and V. A. Saks, Ph.D., Protection of Ischemic Myocardium by Exogenous Phosphocreatine, vol. 94, pp. 762-769 (1987).
D. M. Turner and J. B. Walker—Enhanced Ability of Skeletal Muscle Containing Cyclocreatine Phosphate to Sustain ATP Levels During Ischemia Following B—Adrenergic Stimulation, Journal of Biological Chemistry, vol. 262, pp. 6605-6609 (1987).
James J. Morris, III, M.D., Gary L. Pellom, M.S., Charles E. Murphy, M.D., David R. Salter, M.D., Jacques P. Goldstein, M.D. and Andrew S. Wechsler, M.D., Quantification of the Conractile Response to Injury: Assessment of the Work-Length Relationship in the Intact Heart, vol. 76, No. 3, pp. 717-727 (Sep. 1987).
Mark D. Jacobstein, M.D., Facc. Thomas A. Gerken, Ph.D., Abdul M. Bhat, M.D., Pierre G. Carlier, M.D., Ph.D., Myocardial Protection During Ischemia by Prior Feeding with the Creatine Analog: Cyclocreatine, vol. 14, No. 1, pp. 246-251 (Jul. 1989).

Primary Examiner—Stanley J. Friedman
Attorney, Agent, or Firm—Chilton, Alix & Van Kirk

[57] ABSTRACT

The use of cyclocreatine to preserve and/or restore the physiological functionality of muscle tissue subject to ischemia.

14 Claims, 3 Drawing Sheets

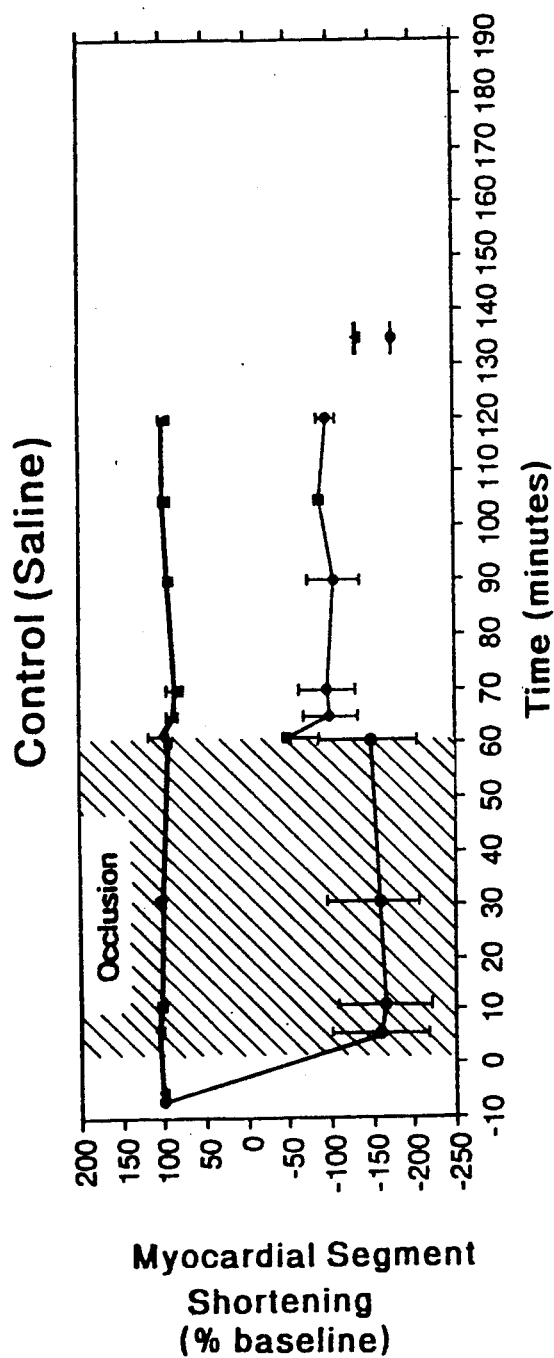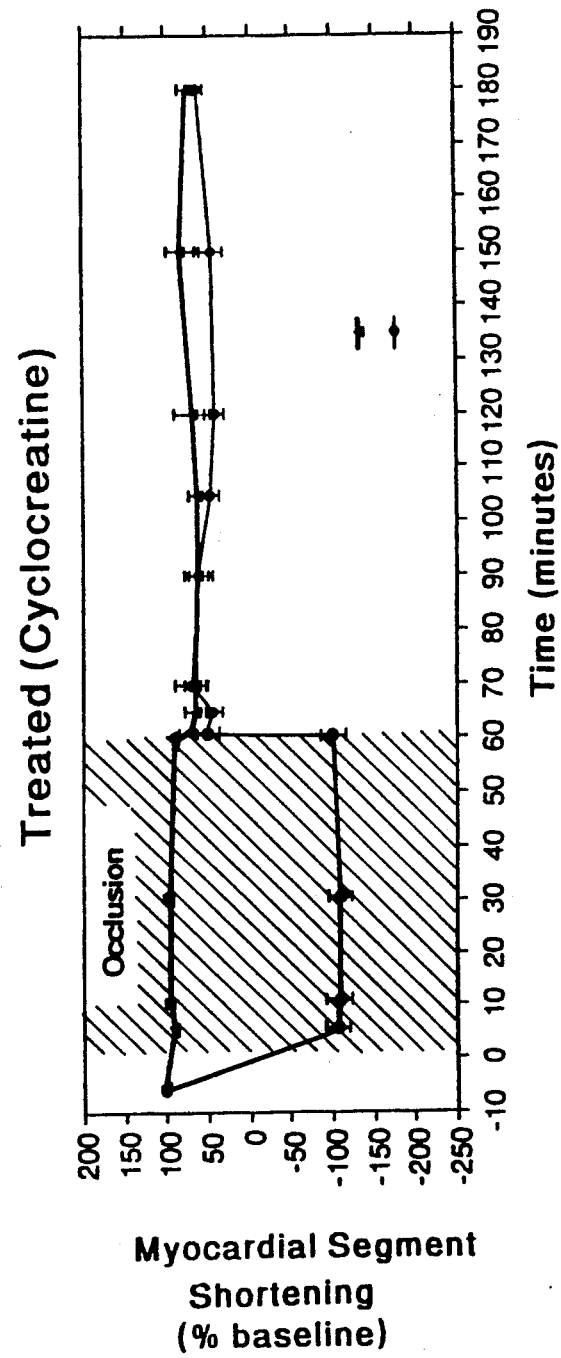

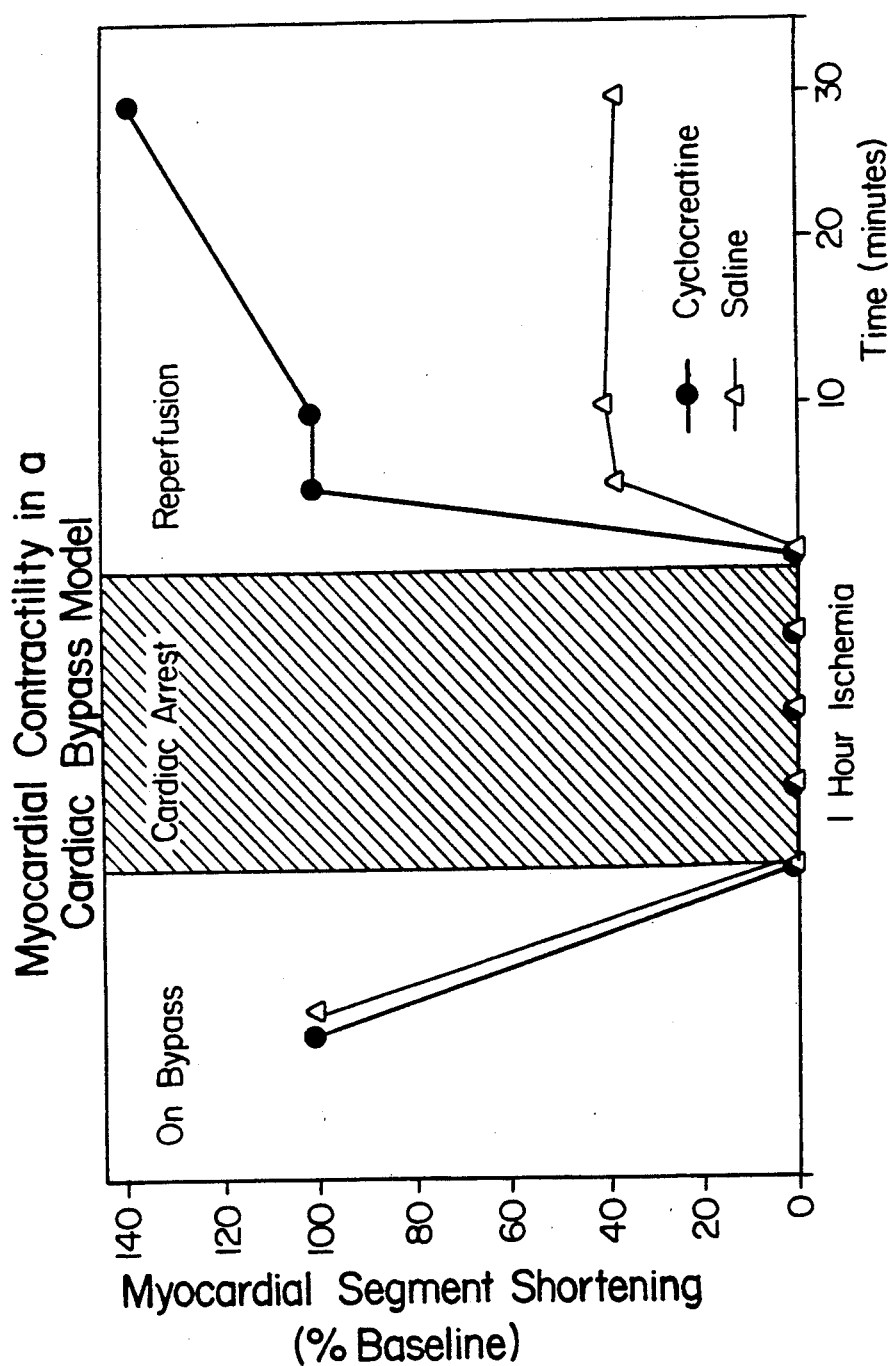

METHOD FOR RESTORING FUNCTIONALITY IN MUSCLE TISSUE

BACKGROUND AND SUMMARY OF THE INVENTION

The present invention relates generally to a method for preserving and/or restoring functionality in muscle tissue subject to ischemia, particularly tissue such as the myocardium subject to reperfusion.

It has been reported by Turner and Walker in J. Biological Chem., Vol. 262, p. 6605-9 (1989) that the dietary ingestion of the creatine analogue cyclocreatine (1-carboxymethyl-2-iminoimidazolidine) imparts to tissue the ability to sustain high levels of myocardial adenosine triphosphate (ATP) or at least to delay the depletion of ATP during total ischemia. The cyclocreatine is reported to be effective provided the dietary supplement is ingested over a period of at least two days prior to the onset of ischemia but achieves a maximum response where the dietary supplement has been provided over a period of about ten to fourteen days prior to onset of ischemia. It is believed this period of time is required in order to permit the dietary supplement, cyclocreatine, to undergo phosphorylation since it is the synthetic phosphagen that is believed to be effective in helping to conserve the total adenylate pool and to buffer the decrease in the ratio of ATP to free adenosine diphosphate (ADP).

Jacobstein et al in J. Am. Coll. Cardial, Vol. 14, p. 246-251 (July 1989) have confirmed that the dietary ingestion of cyclocreatine preserves myocardial ATP during ischemia and also have established that cyclocreatine ingestion delays the development of acidosis and the onset of poor ventricular compliance, as evidenced by a rigor-like increase in tonic pressure, during ischemia. However, it is known that substantial cell damage also can occur during post-ischemic reperfusion and the effect of cyclocreatine on restoring tissue function in an intact muscle tissue model following reperfusion is not known.

Accordingly an object of the present invention is to provide a system for effecting the prompt recovery of tissue function, such as contractility, in muscle tissue during and following post-ischemic reperfusion. Included in this object is the provision for the administration of a creatine analogue such as cyclocreatine to restore contractility function during perfusion in ischemic muscle tissue, particularly to restore and sustain myocardial contractility function in patients with coronary insufficiency. Such a system offers potential for allowing better clinical management of patients with both controlled and uncontrolled ischemic conditions. In the controlled category are those patients with angina or undergoing heart surgery, organ transplant or similar procedures. In the uncontrolled category are those patients that have already experienced myocardial infarct attack. It is believed this treatment also may increase exercise tolerance in patients with known coronary artery disease and increase aortic clamp time tolerance during cardiac surgery. Thus, the treatment can be used as a presurgical procedure or, following a myocardial infarct attack, as a preventative measure to avoid damage otherwise caused by reperfusion and minimize continued ischemic damage after a myocardial infarct.

Other objects and advantages will be in part obvious and in part pointed out more in detail hereinafter.

These and related objects are achieved in accordance with the present invention by providing a method of achieving prompt recovery of functionality in muscle tissue comprising the step of administering, preferably by injection or infusion, an effective amount of cyclocreatine prior to the onset of ischemia, or after myocardial infarct, for restoring and preserving muscle tissue functionality post-ischemia.

A better understanding of the invention will be obtained from the following detailed description and the accompanying drawing as well as from the illustrative applications of the invention, including the process steps and components thereof and the relationship of one or more of such steps or components with respect to each of the others, as well as the features, characteristics, compositions, properties and relation of elements described and exemplified herein.

BRIEF DESCRIPTION OF THE DRAWING

FIGS. 1 and 2 are graphs showing the contractility in ischemic and non-ischemic areas of the heart resulting from an arterial occlusion followed by reperfusion.

FIG. 4 is a graph showing the contractility in hearts arrested for cardiac bypass surgery during ischemia and reperfusion.

DESCRIPTION OF A PREFERRED EMBODIMENT

Figure 3A:
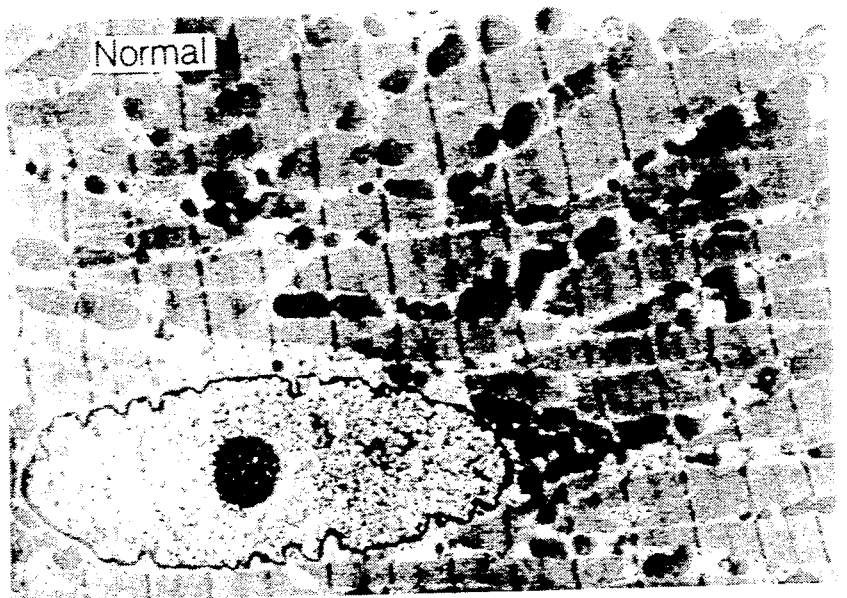
FIGS. 3A-3C is a series of electron microscope photographs of the myocardium of test animals prior to ischemia (3A) and after post-ischemic reperfusion (3B and 3C).

As mentioned, the effect of cyclocreatine on post-ischemic reperfusion functionality and the effect of administering such an injection immediately prior to (e.g. within a few hours or less of) ischemia, is not known. However, according to the present invention it has now been found that the administration of cyclocreatine shortly prior to ischemia, for example, thirty minutes or more prior to an ischemic condition, is effective to restore contractility function. Such administration can have application as a presurgical procedure to prevent loss of contractility associated with post-ischemic reperfusion.

The administration of cyclocreatine preferably is carried out by the most convenient or direct route available. Thus, injection of the material, typically within a fluid carrier such as a sterile saline solution, is usually employed, with intravenous injection being preferred when the treatment involves the cardiovascular system. Where thus employed, administration may be initiated prior to surgery and optionally continued during and following the surgical procedure, although it is believed that only the pre-ischemic administration is fully effective. Such solutions typically have an essentially neutral pH, such as the conventionally employed saline solution. Of course, other appropriate means of administration can be used depending upon the particular tissue of concern and the vehicle used for its administration.

As mentioned, initiation of the treatment should be pre-ischemic to provide the most beneficial result, and use for even very short pre-ischemic time periods can be effective. Use during full ischemia where no pre-ischemic dosage has been administered is not effective. Saline solutions saturated with cyclocreatine at room temperature and administered intravenously have been found to be effective to restore contractility when initiated about thirty minutes or less prior to surgery. However, different concentrations may require different time intervals in order to be effective. Although the temperature of the solution may vary depending on the procedure being employed, it should be consistent with the conditions of that procedure.

In most instances, sterile saline solutions containing substantially more than one percent and typically more than three percent by weight of cyclocreatine have been effective within one half hour of surgery, although somewhat lower percent levels of cyclocreatine may be effective when administered within one to two hours prior to surgery. Where a saturated solution containing about five percent by weight cyclocreatine at room temperature is employed, it has been found to be consistently effective within about thirty minutes and less. Of course, the concentration level at saturation will vary with temperature. The dosage administered may be as low as about 2 grams per 70 kilograms of body weight but typically is greater than about 6 g/70 kg. Excellent results have been achieved at dosage levels of about 8-12 g/70 kg of body weight.

The cyclocreatine employed can be synthesized according to a known procedure as set forth by Griffiths et al in J. Bio. Chem. 1976, Vol. 251, pages 2049-2054. In order to determine the influence of cyclocreatine on the restoration of contractility, test animals such as dogs have been intravenously injected with the cyclocreatine solution shortly prior to surgery, typically within thirty minutes. As controls, other test animals have been similarly intravenously injected with saline solution. Myocardial contractility has been measured prior to ischemia to establish baseline values so that variations from the baseline during ischemia and reperfusion can be easily calculated. In keeping with the present invention it also has been found that cyclocreatine has no appreciable direct effect on not only contractility, but also on heart rate and arterial blood pressure thereby suggesting that cyclocreatine does not exert its action by modulating myocardial function.

The procedure used for measuring contractility is sonomicrometry and provides a measurement of segmental contractility using sets of ultrasonic transducers implanted in ischemic and non-ischemic areas of the heart. As expected, loss of contractility is manifested in all test animals during ischemia. Where the heart is not arrested but only a portion thereof is rendered ischemic by occlusion of the artery feeding that portion, bulging of the heart muscle will also occur.

The procedure employed for measuring contractility generally follows the technique described by Chitwood et al in J. Thorac, Cardiovac Surg., Vol. 80, p. 724-35 (1980). In accordance with that technique two pairs of ultrasonic dimensional transducers are implanted in a circumferential plane, one pair at an area to be subject to ischemia and the other pair in an area not subject to ischemia. The ischemic area employed is the ventricle fed by the left anterior descending (LAD) coronary artery and the transducer crystals are placed in the LAD-fed area distal to the point of occlusion. The non-ischemic area is the left ventricular lateral wall. The crystals are connected to a sonomicrometer and changes in the distance between the crystals are recorded using simultaneous tracing equipment. Myocardial contractility is recorded prior to ischemia and during ischemia and reperfusion. Myocardial segment shortening is calculated as a percent of the baseline of active contraction measured pre-ischemia, with negative percentage values being indicative of passive muscle bulging.

FIGS. 1 and 2 illustrate the dramatic difference in the restoration of contractility function in ischemic myocardium during reperfusion. Both graphs plot contractility, as a percent of the baseline value, during ischemia and reperfusion for control (FIG. 1) and cyclocreatine treated (FIG. 2) test animals. Loss of myocardial contractility was recorded during ischemia at $-156\%$ of baseline for the control and $-116\%$ for cyclocreatine treated animals thereby manifesting muscle bulging in both instances. The immediate recovery of the cyclocreatine treated animals following reperfusion is clearly evidenced in FIG. 2 with a rise to 82% of baseline, as is the continuation of this muscle function through the entire reperfusion period. It will be noted that this recovery during reperfusion took place almost immediately. The control animals did not show active contraction during reperfusion and continued to show passive muscle bulging (note the value of $-91\%$ of baseline).

Upon completion of reperfusion the depletion of ATP and CP were determined relative to normal pre-ischemic levels. Some depletion has been found but the depletion is significantly less in the cyclocreatine treated tissue than in the control tissue. While this data is consistent with the results reported by Jacobstein et al, mentioned hereinbefore, it is not clear that the preservation of high levels of ATP fully explains the observed restoration of contractility during reperfusion.

The following examples are given in order that the effectiveness of the present invention may be more fully understood. These examples are set forth for the purpose of illustration only and are not intended in any way to limit the practice of the invention. Unless otherwise specified, all parts are given by weight.

EXAMPLE I

Twelve adult male dogs (20-25 kg) were anesthetized with sodium pentobarbital (30 mg/kg) and maintained on an endotracheal tube attached to a Harvard respirator pump. Through a left thoracotomy (5th intercostal space), the hearts were exposed and the left anterior descending (LAD) coronary artery was occluded for 1 hour using 2-0 silk in double ligation. Heparin sulfate (2500-3000 IU) was injected intravenously prior to LAD occlusion. Ligation was released after 1 hour of ischemia, and hearts were perfused for an additional 2 hours.

Cyclocreatine (1-carboxymethyl-2-iminoimidazolidine) was synthesized and the purity and physical characteristics of cyclocreatine were verified using nuclear magnetic resonance (NMR). Six dogs were injected intravenously with 120 ml of a 5% cyclocreatine solution (prepared in sterile saline) 30 minutes prior to surgery and with 50 ml every 30 minutes during ischemia and reperfusion. Six control dogs received an intravenous infusion of saline during occlusion and reperfusion.

The pericardium was opened and an arterial line was obtained by inserting an aortic catheter at the root of the aorta. Segmental myocardial function was measured using two pairs of Piezo ultrasonic crystals implanted in a circumferential plane. One pair (1 cm apart) was placed at the LAD-fed area adjacent the occlusion (the ischemic area), while the other was at a non-LAD-fed area (left ventricular lateral wall). Changes in the distance between the crystals were recorded using the Honeywell simultrace. Myocardial segment shortening was calculated as a percent of baseline of active contraction measured before occlusion. Baseline values of contractility, heart rate, and arterial blood pressure were obtained before and after administration of cyclocreatine prior to surgery. It was determined that there is no direct effect of cyclocreatine on these parameters.

The results of ischemia and reperfusion on contractility are set forth in the following table and in FIGS. 1 and 2, showing restoration of active contraction during reperfusion for cyclocreatine treated dogs while the control dogs did not show active contraction during reperfusion and continued to show passive muscle bulging.

TABLE 1

MYOCARDIAL CONTRACTILITY MEASURED IN ISCHEMIC AREAS DURING REPERFUSION
(percent of non-ischemic areas)

| Reperfusion Time (minutes) | Saline | Cyclocreatine |
|---|---|---|
| 1 | $-48 \pm 14$ | $70 \pm 9$ |
| 10 | $-111 \pm 18$ | $88 \pm 13$ |
| 30 | $-111 \pm 28$ | $100 \pm 22$ |
| 60 | $-95 \pm 8$ | $69 \pm 7$ |
| 120 | | $85 \pm 5$ |

At the end of the 2 hour reperfusion, biopsies (300–500 mg) were obtained from ischemic areas of cyclocreatine-treated and control hearts. The biopsy samples were immediately immersed in liquid nitrogen and stored at $-70°$ C. Myocardial ATP and creatine phosphate (CP) in the samples were measured using high performance liquid chromatography (HPLC). Three biopsy specimens taken from each dog sample were homogenized in 6% perchloric acid using a polytron tissue homogenizer, centrifuged, neutralized to pH 7.0 with 5M potassium carbonate, and filtered for assay on HPLC. Running each extract twice, a volume of 25 ul of a filtered and neutralized perchloric acid extract was injected onto a Nova-Pak $C_{18}$ column. The average levels of pre-ischemic myocardial nucleotides (umoles/gm wet wt) were $6.54 \pm 0.02$ for ATP and $11.87 \pm 0.56$ for Cp. The average ATP and CP levels of cyclocreatine treated dogs showed less depletion following reperfusion as compared with the controls. The average ATP measurement of $5.42 \pm 0.15$ was 83% of pre-ischemic levels for cyclocreatine treated dogs versus $4.26 \pm 0.32$ or 65% for controls. This difference in ATP levels is considered statistically significant ($P < 0.01$). The average CP levels were 97% ($11.69 \pm 1.0$) for treated dogs versus 82% ($9.98 \pm 1.07$) for the controls.

Figure 3B:
Figure 3C:
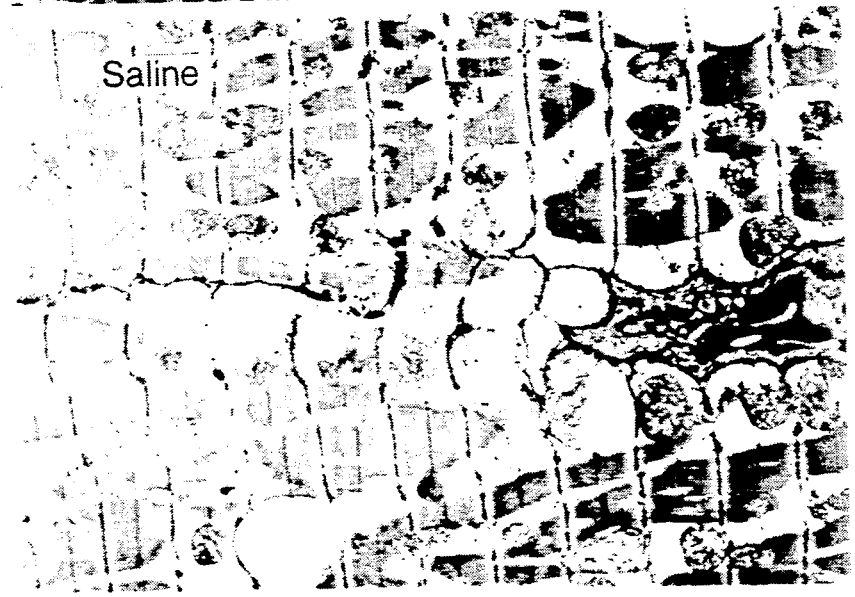

Biopsy samples were taken from ischemic areas of cyclocreatine-treated and control hearts and preserved in 3% glutaraldehyde in buffer prior to processing for electron microscopy. Analysis of myocardial cells of both groups (i.e., mitochondria, cell edema, nucleus, etc.) was performed blindly. Electron microscopy analysis showed significantly less myocardial cell damage in the cyclocreatine treated dogs compared to the controls, as clearly shown in the series of photographs designated FIG. 3. The top photo (FIG. 3A) shows a normal myocardium tissue specimen while FIGS. 3B and 3C show reperfused myocardium tissue specimens that received pre-ischemic treatments with cyclocreatine and saline, respectively. The photographs show significantly less myocardial cell damage (i.e. intra- and inter-myofibrillar edema and mitochondrial swelling and injury) in the cyclocreatine treated test animals (FIGS. 3B) than in the saline treated controls (FIGS. 3C).

EXAMPLE II

In an attempt to show the effect of cyclocreatine on patients undergoing open heart surgery involving myocardial revascularization, change of valves or the like, this example explores post-ischemic myocardial contractility in a canine model.

Adult mongrel dogs (15–20 kg) were treated with cyclocreatine and saline as in Example I, the dogs underwent open heart surgery and cardiac arrest for 1 hour followed by reperfusion for 2 hours. The dogs were anesthetized with sodium pentobarbital (30 mg/kg) and maintained on an endotracheal tube attached to a Harvard respirator pump. Following exposure of the heart, an arterial line was obtained through cannulation of the ascending aorta. A venous line was obtained through cannulation of the right atrium. The animals then were placed on cardiopulmonary bypass (i.e. a pump and an oxygenator), and the heart was connected to a perfusion pump. Cold crystalloid cardioplegia was injected as a first bolus of 350 ml to arrest the heart, followed by consecutive injections (150 mg each) 20 min apart. The cardioplegia solution was composed of 1 liter of plasmalyte containing 30 ml dextrose 50%, 20 mg. potassium chloride, 24 mg sodium bicarbonate, 20 IU of soluble insulin, and 2 mg calcium chloride. During the 1 hour arrest, the heart temperature was maintained bellow $18°$ C. and the body temperature bellow $25°$ C.

Segmented myocardial contractility was measured using the procedure of Example I. As shown in FIG. 4, upon reperfusion following global myocardial ischemia the contractility of the cyclocreatine treated dog immediately returned to its baseline level while that of the control only moved to 40% of baseline and remained level.

As can be seen from the foregoing detailed description, administration of cyclocreatine can provide a definite benefit to patients experiencing myocardial ischemia such as those undergoing open heart surgery or heart transplant as well as to myocardial infarct patients by facilitating recovery of myocardial function following post-ischemic reperfusion.

As will be apparent to persons skilled in the art, various modifications, adaptations and variations of the foregoing specific disclosure can be made without departing from the teachings of the present invention.

I claim:

1. A method of preserving and/or restoring the physiological functionality of in vivo animal muscle tissue subject to ischemia comprising the step of administering cyclocreatine in an amount effective for restoring post-ischemic physiological function to said tissue to a substantially pre-ischemic level.

2. The method of claim 1 wherein the cyclocreatine is dispersed in a fluid carrier prior to being administered.

3. The method of claim 1 wherein the cyclocreatine is dissolved in a liquid carrier having an essentially neutral pH.

4. The method of claim 1 wherein the cyclocreatine is dispersed in a carrier at a concentration substantially greater than one percent by weight.

5. The method of claim 4 wherein the concentration is about three percent by weight or more.

6. The method of claim 4 wherein the concentration is about five percent by weight.

7. The method of claim 4 wherein the concentration of cyclocreatine is sufficient to saturate the carrier at room temperature.

8. The method of claim 1 wherein the cyclocreatine is administered at a dosage level in excess of 2 grams per 70 kilograms of body weight.

9. The method of claim 1 wherein the cyclocreatine is administered at a dosage level greater than 6 grams per 70 kilograms of body weight.

10. The method of claim 1 wherein the cyclocreatine is administered prior to ischemia.

11. The method of claim 1 wherein the initiation of administration is at least about one half hour prior to ischemia.

12. The method of claim 1 wherein the administration continues during reperfusion.

13. The method of claim 1 wherein the muscle tissue is myocardial tissue and the administration is carried out prior to ischemia and reperfusion.

14. The method of claim 1 wherein the cyclocreatine is administered by injection.

* * * * *